US005877161A

United States Patent [19]
Riabowol

[11] Patent Number: 5,877,161
[45] Date of Patent: *Mar. 2, 1999

[54] CYCLIN D1 NEGATIVE REGULATORY ACTIVITY

[75] Inventor: Karl T. Riabowol, Calgary, Canada

[73] Assignee: University Technologies International Inc., Calgary, Canada

[*] Notice: This patent issued on a continued prosecution application filed under 37 CFR 1.53(d), and is subject to the twenty year patent term provisions of 35 U.S.C. 154(a)(2).

[21] Appl. No.: 602,019

[22] Filed: Feb. 15, 1996

Related U.S. Application Data

[62] Division of Ser. No. 394,562, Feb. 28, 1995, Pat. No. 5,514,571, and a continuation of Ser. No. 102,219, Aug. 5, 1993, abandoned.

[51] Int. Cl.[6] .................................................... A61K 48/00
[52] U.S. Cl. .......................................... 514/44; 435/172.3
[58] Field of Search ........................ 435/6, 172.1, 172.3; 514/44

[56] References Cited

FOREIGN PATENT DOCUMENTS

WO92/15603  3/1992  WIPO.
WO92/20796  5/1992  WIPO.

OTHER PUBLICATIONS

Verma et al. *Nature*, vol. 389, 1997, pp. 239–242.
*Nature Biotechnology*, vol. 15, 1997, p. 815.
Baldin, B., et al. G. "Cyclin D1 is a nuclear protein required for cell cycle progression in $G_1$" *Genes & Development* 7: 812–821 (1993).
Dowdy, S.,F., et al. "Physical Interaction of the Retinoblastoma Protein with Human D Cyclins", *Cell* 73: 499–511 (1993).
Draetta, G., "Cell cycle control in eukaryotes: molecular mechanisms of cdc2 activation", *Trends Biol. Sci.* 15: 378–383 (1990).
Dulic, V., et al. "Association of Human Cyclin E with a Periodic $G_1$–S Phase Protein Kinase", *Science* 257: 1958–1961 (1992).
Ewen, M.E., et al. "Functional Interactions of the Retinoblastoma Protein with Mammalian D–type Cyclins," *Cell* 73: 487–497 (1993).
Faust, J.B. et al. "Amplification and Expression of the bcl–1 Gene in Human Solid Tumor Cell Lines", *Cancer Res.* 52: 2460–2463 (1992).
Giordano, A. et al., "A 60 kd cdc2–Associated Polypeptide Complexes with the E1A Proteins in Adenovirus–Infected Cells"; *Cell* 58, 981–990 (1989).
Girard, F., et al., "Cyclin A is Required for the Onset of DNA Replication in Mammalian Fibroblasts", *Cell* 67: 1169–1179 (1991).
Goldstein, S., "Replicative Senescence: The Human Fibroblast Comes of Age", *Science* 249: 1129–1133 (1990).
Hayflick, L. et al., "The Serial Cultivation of Human Diploid Cell Strains[1]", *Exp. Cell Res.* 25: 585–621 (1961).
Hayflick, L., "The Limited In Vitro Lifetime of Human Diploid Cell Strains[1,2]", *Exp. Cell Res.* 37: 614–636 (1965).
Hinds, P.W. et al., "Regulation of Retinoblastoma Protein Functions by Ectopic Expression of Human Cyclins", *Cell* 70: 993–1006 (1992).
Jiang, W. et al., "Amplification and Expression of the Human Cyclin D Gene in Esophageal Center[1], *Cancer Res.* 52: 2980–2983 (1992).
Kiyokawa, H. et al., "Cloning of a D–type cyclin from murine erythroleukemia cells", *Proc. Natl. Acad. Sci.* 89: 2444–2447 (1992).
Koff, A., et al., "Formation and Activation of a Cyclin E–cdk2 Complex During the $G_1$ Phase of the Human Cell Cycle", *Cell* 66: 1217–1228 (1991).
Koff, A., et al., "Negative Regulation of G1 in Mammalian Cells: Inhibition of Cyclin E–Dependent Kinase by TGF–$\beta$", *Science* 260: 536–539 (1993).
Koff, A. et al., "Human Cyclin E, a New Cyclin that Interacts with Two Members of the CDC2 Gene Family", *Science* 257: 1689–1694 (1992).
Lamb, N.J.C., et al., "Microinjection of p34 $^{cdc2}$ Kinase Induces Marked Changes in Cell Shape, Cytoskeletal Organization, and Chromatin Structure in Mammalian Fibroblasts", *Cell* 60: 151–165 (1990).
Lew, D.J., et al., "Isolation of Three Novel Human Cyclins by Rescue of G1 Cyclin (Cln) Function in Yeast", *Cell* 66: 1197–1206 (1991).
Matsushime, H., et al., "Identification and Properties of an Atypical Catalytic Subunit (p34$^{PSK-J3}$/cdk4) for Mammalian D Type G1 Cyclins", *Cell* 65: 701–713 (1991).
Matsushime, H. et al., "Colony–Stimulating Factor 1 Regulates Novel Cyclins During the G1 Phase of the Cell Cycle", *Cell* 71: 323–334 (1992).
Motokura, T. et al., "A novel cyclin encoded by a bc/1–linked candidate oncogene", *Nature* 350: 512–515 (1991).
Ohtsubo, M., et al., "Cyclin–Dependent Regulation of $G_1$ in Mammalian Fibroblasts", *Science* 259: 1908–1912 (1993).
Pagano, M., et al., "Cyclin A is required at two points in the human cell cycle", *EMBO J.* 11: 961–971 (1992).
Pines, J., et al., "Human cyclin A is adenovirus E1A–associated protein p60 and behaves differently from cyclin B", *Nature* 346: 760–763 (1990).
Quelle, D.E., et al., "Overexpression of mouse D–type cyclins accelerates $G_1$ phase in rodent fibroblasts", *Genes & Development* 7: 1559–1571 (1993).
Riabowol, K.T. et al., , "The catalytic subunit of CAMP–dependent protein kinase induces expression of genes containing CAMP–responsive enhancer elements", *Nature* 336: 83–86 (1988).

(List continued on next page.)

*Primary Examiner*—James Ketter
*Attorney, Agent, or Firm*—Burns, Doane, Swecker & Mathis, L.L.P.

[57] ABSTRACT

Use of cyclin D1 as a negative regulator of cell proliferation is disclosed. Overexpression of cyclin D1 blocks cell growth, while blocking cyclin D1 expression promotes cell proliferation.

6 Claims, 9 Drawing Sheets

OTHER PUBLICATIONS

Riabowol, K.T., et al., "Transcription factor AP–1 activity is required for initiation of DNA synthesis and is lost during cellular aging", *Proc. Natl. Acad. Sci.* 89: 157–161 (1992).

Riabowol, K.T., et al., "The cdc2 Kinase Is a Nuclear Protein That Is Essential for Mitosis in Mammalian Cells", *Cell* 57: 393–401 (1989).

Richter, K.H. et al., "Down–Regulation of cdc2 in Senescent Human and Hamster Cells", *Cancer Res.* 51: 6010–6013 (1991).

Rosenthal, E.T., et al., "Selective Translation of mRNA Controls the Pattern of Protein Synthesis during Early Development of the Surf Clam, Spisula solidissima", *Cell* 20: 487–494 (1980).

Stein, G.H., et al., "Senescent cells fail to express cdc2, cycA, and cycB in response to mitogen stimulation", *Proc. Natl. Acad. Sci. USA* 88: 11012–11016 (1991).

Tsai, L–H., et al., "The cdk2 kinase is requird for the G1–to–S transition in mammalian cells", *Oncogene* 8: 1593–1602 (1993).

Tsai, L–H., et al., "Isolation of the human cdk2 gene that encodes the cyclin A–and adenovirus E1A–associated p33 kinase", *Nature* 353: 174–177 (1991).

Walker, D.H., et al., "Role for cyclin A in the dependence of mitosis on completion of DNA replication", *Nature* 354: 314–317 (1991).

Withers, D.A. et al. "Characterization of a Candidate bcl–1 Gene", *Mol. Cell Biol.* 11: 4846–4853 (1991).

Won, K–A., et al., "Growth–regulated expression of D–type cyclin genes in human diploid fibroblasts", *Proc. Natl. Acad. Sci.* 89: 9910–9914 (1992).

Xiong, Y., et al., "Human D–Type Cyclin", *Cell* 65: 691–699 (1991).

Xiong, Y., Zhang, et al., "D Type Cyclins Associate with Multiple Protein Kinases and the DNA Replication and Repair Factor PCNA", *Cell* 71: 505–514 (1992).

Xiong, Y., et al. "Subunit rearrangement of the cyclin–dependent kinases is associated with cellular transformation", *Genes & Development* 7: 1572–1583 (1993).

Yang, Y., Raper, et al., "An approach for treating the hepatobility disease of cystic fibrosis by somatic gene transfer", *Proc. Nat'l Acad. Sci. USA* 90: 4601–4605 (1993).

Zindy, F. et al. "Cyclin A is Required In S Phase In Normal Epithelial Cells", *Biophys. Res. Commun.* 182: 1144–1154 (1992).

Orkin et al., *Report and Recommendations of the Panel to Access the NIH Investment in Research on Gene Therapy*, 1995, NIH.

Benoit et al., *Curr. Eye Res.*, vol. 9 (Suppl.), 1990, pp. 201–205.

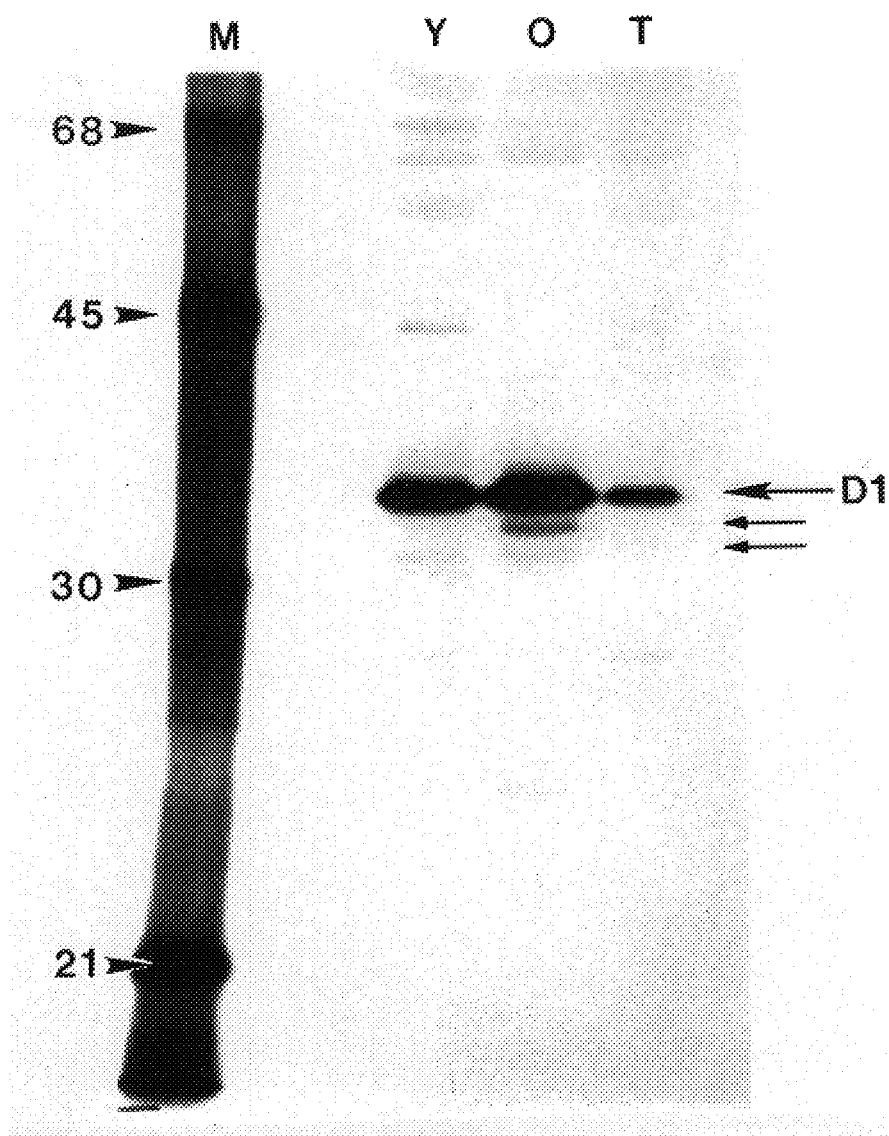

FIG. 5A
FIG. 5B
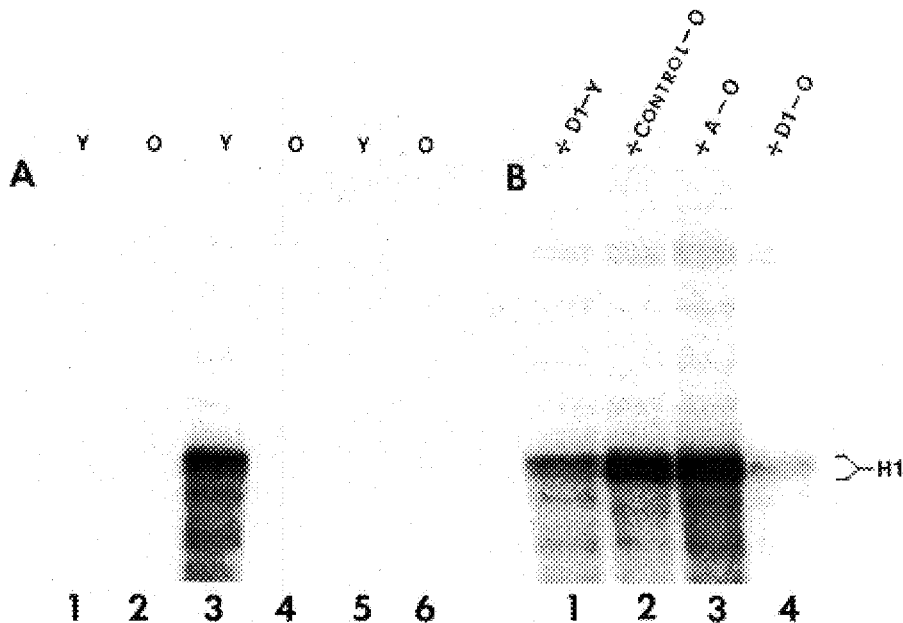
FIG. 5C
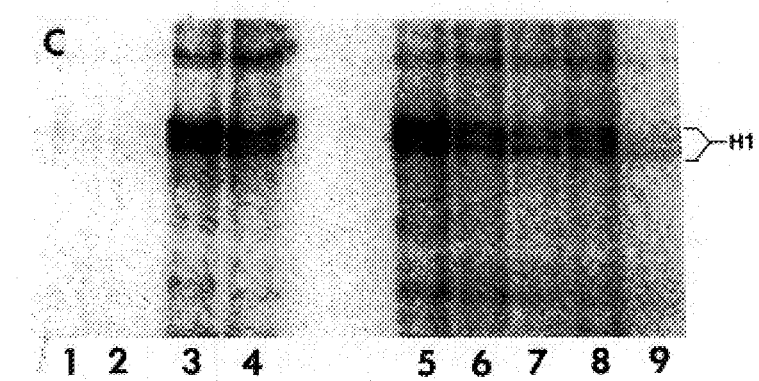

FIG. 6A
FIG. 6B
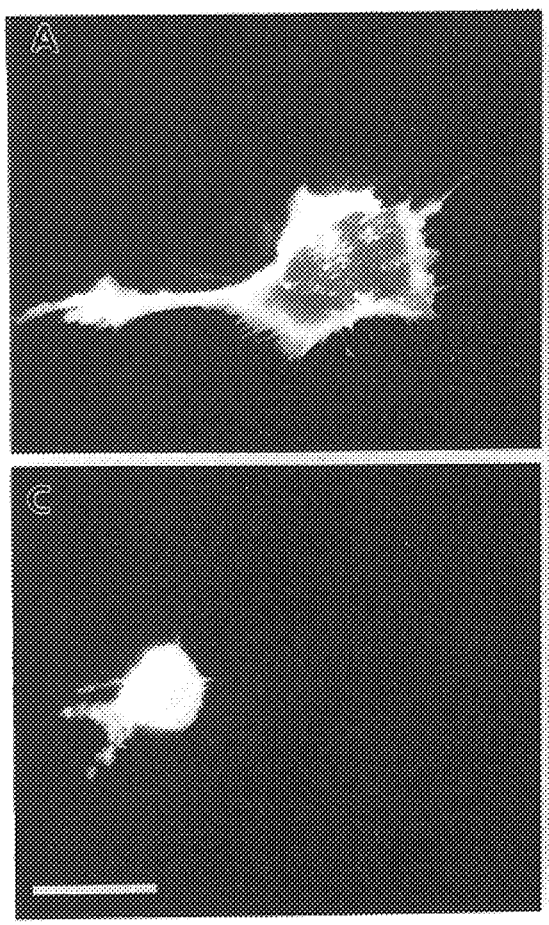
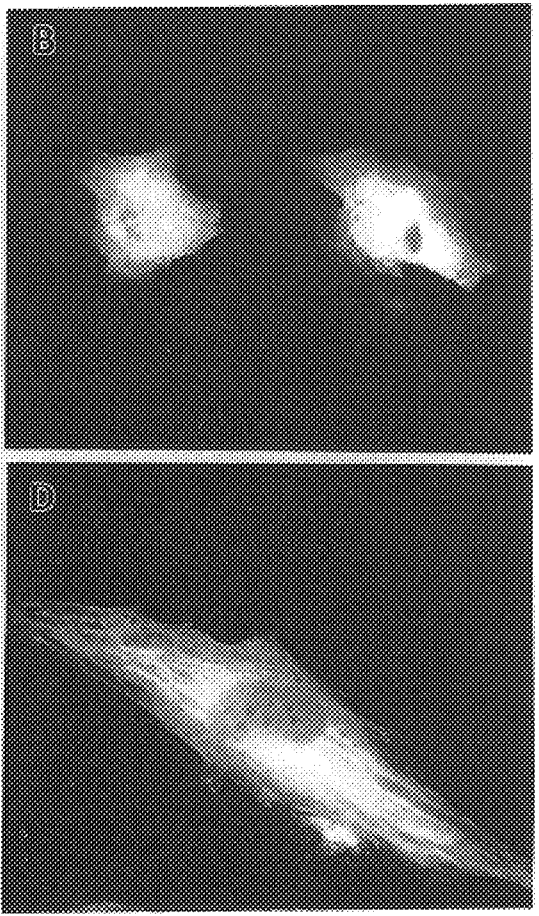
FIG. 6C
FIG. 6D

FIG. 7A
FIG. 7B
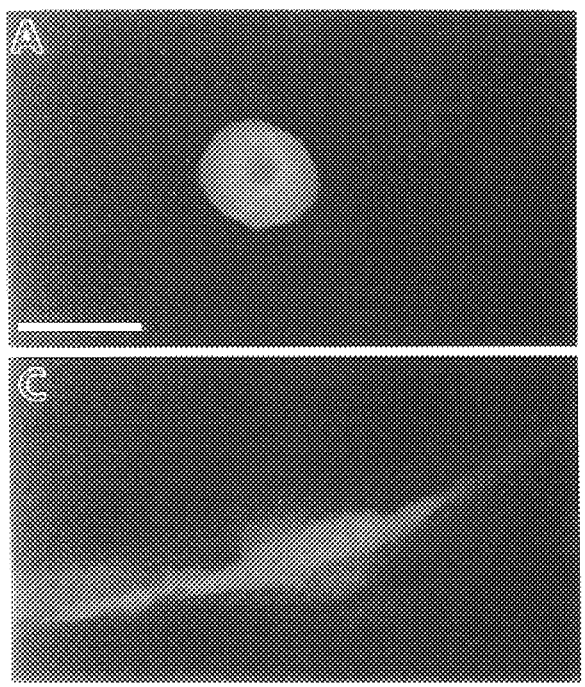
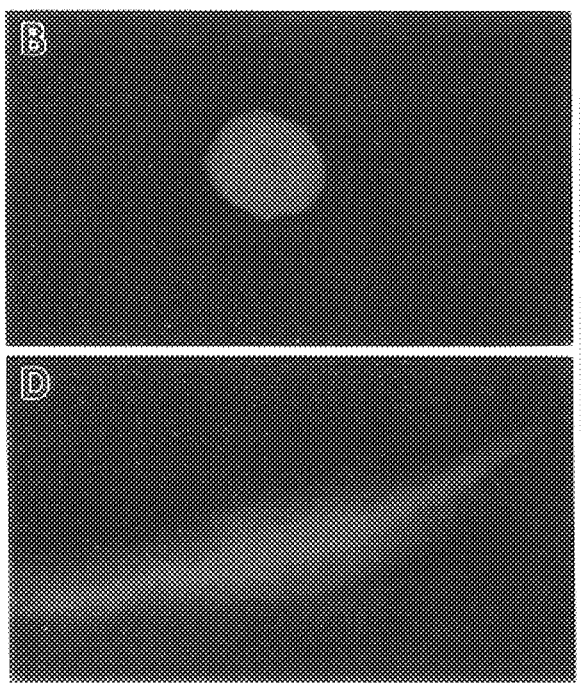
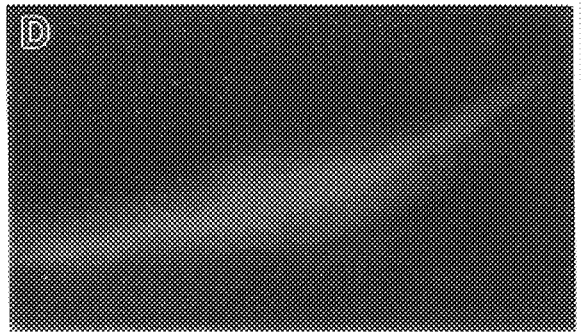
FIG. 7C
FIG. 7D

CYCLIN D1 NEGATIVE REGULATORY ACTIVITY

This application is a divisional of application Ser. No. 08/394,562, filed Feb. 28, 1995, now U.S. Pat. No. 5,514,571, which is a continuation of application Ser. No. 08/102,219 filed Aug. 5, 1993, abandoned.

FIELD OF THE INVENTION

The present invention relates to cyclin D1 as a regulator of cell proliferation.

References

The following references are cited in the application as numbers in parenthesis at the relevant portion of the application.

1. Rosenthal, E. T., Hunt, T. and Ruderman, J. V. *Cell* 20, 487–494 (1980).
2. Riabowol, K. T., Draetta, G., Brizuela, L., Vandre, D. and Beach, D. *Cell* 57, 393–401 (1989).
3. Draetta, G. *Trends Biol. Sci.* 15, 378–383 (1990).
4. Giordano, A. et al. *Cell* 58, 981–990 (1989).
5. Pines, J. and Hunter, T. *Nature* 346, 760–763 (1990).
6. Tsai, L-H., Harlow, E. and Meyerson, M. *Nature* 353, 174–177 (1991).
7. Girard, F., Strausfeld, U., Fernandez, H. and Lamb, J. *Cell* 67, 1169–1179 (1991).
8. Walker, D. H. and Maller, J. L. *Nature* 354, 314–317 (1991).
9. Pagano, M., Peppercock, P., Verde, F., Ansorge, W. and Draetta, G. *EMBO J.* 11, 961–971 (1992).
10. Zindy, F. et al. *Biophys. Res. Commun.* 182, 1144–1154 (1992).
11. Tsai, L-H., Lees, E., Faha, B., Harlow, E. and Riabowol, K. *Oncogene* 8, 1593–1602 (1993).
12. Xiong, Y., Connolly, T., Futcher, B. and Beach, D. *Cell* 65, 691–699 (1991).
13. Koff, A., Cross, F., Fisher, A., Schumacher, J., Leguellec, K., Philippe, M. and Roberts, J. M. *Cell* 66, 1217–1228 (1991).
14. Lew, D. J., Dulic, V. and Reed, S. I. *Cell* 66, 1197–1206 (1991).
15. Dulic, V., Lees, E. and Reed, S. I. *Science* 257, 1958–1961 (1992).
16. Koff, A. et al. *Science* 257, 1689–1694 (1992).
17. Motokura, T. et al. *Nature* 350, 512–515 (1991).
18. Withers, D. A. et al. *Mol. Cell Biol.* 11, 4846–4853 (1991).
19. Matsushime, H., Roussel, M. F., Ashmun, R. A. and Sherr, C. J. *Cell* 65, 701–713 (1991).
20. Kiyokawa, H. et al. *Proc. Natl. Acad. Sci.* 89, 2444–2447 (1992).
21. Faust, J. B. and Meeker, T. C. *Cancer Res.* 52, 2460–2463 (1992).
22. Jiang, W. et al. *Cancer Res.* 52, 2980–2983 (1992).
23. Xiong, Y., Zhang, H. and Beach, D. *Cell* 71, 505–514 (1992).
24. Hayflick, L. and Moorhead, P. S. *Exp. Cell Res.* 25, 585–621(1961).
25. Hayflick, L. *Exp. Cell Res.* 37, 614–636 (1965).
26. Goldstein, S. *Science* 249, 1129–1133 (1990).
27. Won, K-A., Xiong, Y., Beach, D. and Gilman, M. Z. *Proc. Natl. Acad. Sci.* 89, 9910–9914 (1992).
28. Matsushime, H. et al., *Cell* 71, 323–334 (1992).
29. Richter, K. H. et al. *Cancer Res.* 51, 6010–6013 (1991).
30. Stein, G. H., Drullinger, L. F., Robetorye, R. S., Pereira-Smith, O. M. and Smith, J. R. *Proc. Natl. Acad. Sci. USA* 88, 11012–11016 (1991).
31. Riabowol, K. T. et al. *Nature* 336, 83–86 (1988).
32. Lamb, N. J. C., Fernandez, A., Watrin, A., Labbe, J. C. and Cavadore, J. C. *Cell* 60, 151–165 (1990).
33. Hinds, P. W., Mittnacht, S., Dulic, V., Arnold, A., Reed, S. and Weinberg, R. *Cell* 70, 993–1006 (1992).
34. Riabowol, K. T., Schiff, J. and Gilman, M. Z. *Proc. Natl. Acad. Sci.* 89, 157–161 (1992).
35. Ewen, M. E., Sluss, H. K., Sherr, C. J. Matsushime, H., Kato, J. and Livingston, M. D. *Cell* 73487–497 (1993).
36. Dowdy, S., F., Hinds, P. W., Louie, K., Reed, SI., Arnold, A. and Weinberg, R. A. *Cell* 73, 499–511 (1993).
37. Koff, A., Ohtsuki, M., Polyak, K., Roberts, J. M. and Massague, J. *Science* 260, 536–539 (1993).
38. Arnold, A. International Publication No. WO 92/15603 (PCT/US92/01925) (1992).
39. Beach, D. International Publication No. WO 92/20796 (PCT/US92/04146) (1992).
40. Baldin, B., Lukas, J., Marcote, M. J., Pagano, M. and Draetta, G. *Genes & Development* 7, 812–821 (1993).
41. Yang, Y., Raper, S. E., Cohn, J. A., Engelhardt, J. F. and Wilson, J. M. *Proc. Natl. Acad. Sci. USA* 90, 4601–4605 (1993).

The disclosures of the above publications and patent applications are herein incorporated by reference in their entirety to the same extent as if the language of each individual publication were specifically and individually included herein.

BACKGROUND OF THE INVENTION

A typical cell cycle of a eukaryotic cell includes the M phase, which includes nuclear division (mitosis) and cytoplasmic division or cytokinesis and interphase, which begins with the G1 phase, proceeds into the S phase and ends with the G2 phase, which continues until mitosis begins, initiating the next M phase. In the S phase, DNA replication and histone synthesis occurs, while in the G1 and G2 phases, no net DNA synthesis occurs, although damaged DNA can be repaired. There are several key changes which occur during the cell cycle, including a critical point in the G1 phase called the restriction point or start, beyond which a cell is committed to completing the S, G2 and M phases.

Onset of the M phase appears to be regulated by a common mechanism in all eukaryotic cells. A key element of this mechanism is the protein kinase $p34^{cdc2}$, whose activation requires changes in phosphorylation and interaction with proteins referred to as cyclins, which also have an ongoing role in the M phase after activation.

Cyclins A and B were first identified in marine invertebrates as proteins that underwent periodic cycles of synthesis and degradation, with synthesis occurring during the S and $G_2$ phases of the cell cycle followed by their abrupt degradation during mitosis (1). It is now well established that cyclin B, in association with its kinase catalytic subunit cdc2, plays a critical role in regulating the $G_2$/M transition in mammalian cells (2,3 and references therein). While cyclin A can substitute for cyclin B to produce an active cyclin A/cdc2 kinase, this cyclin also interacts with the related kinase cdk2 (4–6) and most probably provides a function required for the completion of DNA synthesis (7–11).

Several other mammalian cyclins designated C, D1 and E have been isolated based on their ability to complement yeast strains containing conditional $G_1$ cyclin (CLN) genes (12–14). Although human cyclins A and B were also capable of complementing CLN function in yeast (14), cyclin E has recently been reported to associate with the cdk2 kinase during $G_1$ of the cell cycle (11, 15, 16) and cyclin E/cdk2 activity appears to be necessary for entry of human fibroblasts into S phase (11). Reverse genetics was also used to identify cyclin D1 (designated PRAD 1) as a gene translocated by chromosomal inversion adjacent to the regulatory region of the parathyroid hormone gene in parathyroid adenomas (17) and in B cell leukemias and lymphomas (18). The lack of cyclin D1 mRNA expression in myeloid and lymphoid cell lines varied, but generally low levels of expression in a variety of established cell lines (18–22) suggested that inappropriate expression of this cyclin might contribute to unregulated cell growth.

Based on sequence comparisons with cyclins A, B, C and E, and the isolation of additional related cyclins D2 and D3 (originally designated CYL2 and CYL3) by low stringency hybridization with cyclin D1 probes (19, 20), it now appears that the D-type cyclins represent a distinct family of proteins (12, 19). Unlike other known cyclins, immune complexes isolated with cyclin D1 antibodies were reported to lack detectable histone H1 or casein kinase activity (19), suggesting that perhaps this cyclin played a role within the cell distinct from the proposed role of other classes of cyclins. In addition, we and others (23) had noted that primary diploid cells that were capable of entering fully a state of quiescence in response to growth factor deprivation, expressed higher levels of this cyclin than transformed cells.

D-type cyclins, including cyclin D1/prad1, have been identified and isolated (38, 39). These were thought to serve as control elements for the start of the cell cycle by activating, in the G1 phase, a protein kinase which is essential for cell cycle start (39). Other researchers have presented evidence that cyclin D1 is involved in the G1-S phase transition in normal fibroblasts (40).

A better understanding of the elements involved in cell cycle regulation and of their interactions would contribute to a better understanding of cell proliferation. These cell cycle regulators could be used to alter or control the process of cell proliferation.

SUMMARY OF THE INVENTION

The present invention relates to the unexpected discovery that cyclin D1 exhibits negative regulatory activity. It appears that, unlike other cyclin molecules which activate kinase activity, cyclin D1 inhibits the activity of the cyclin-dependent kinase cdk2. Normal diploid cells that express high levels of cyclin D1 are unable to enter S phase in response to normally mitogenic stimuli. Thus, an inverse correlation is seen between endogenous cyclin D1 levels and the ability of cells to enter and exit the cell cycle.

We found that the expression of cyclin D1 is highly correlated with maintaining cells in a state of quiescence. Overexpression of cyclin D1 blocks cell growth directly. On the other hand, blocking cyclin D1 expression promotes proliferation of cells.

Accordingly, one aspect of the invention provides a method for increasing proliferation of mammalian cells comprising selecting said mammalian cells whose proliferation is to be increased and decreasing the expression of cyclin D1 in said mammalian cells.

Another aspect of the invention provides a method for decreasing proliferation of mammalian cells comprising selecting said mammalian cells whose proliferation is to be decreased and increasing the expression of cyclin D1 in said mammalian cells.

Yet another aspect of the invention provides a method of detecting a state of quiescence, hyperplasticity or neoplasia in a biological sample comprising obtaining said biological sample; contacting said biological sample with at least one antibody to cyclin D1; detecting the binding of said at least one antibody with cyclin D1 in order to indicate an amount of cyclin D1 expressed by the cells of said biological sample; determining said indicated amount of cyclin D1 in said cells of said biological sample; selecting said biological sample whose cells express a less than normal indicated amount of cyclin D1 as exhibiting a state selected from the group consisting of hyperplasticity and neoplasia; selecting said biological sample whose cells express a greater than normal indicated amount of cyclin D1 as exhibiting a state of quiescence; and determining on the basis of the selection in the two previous selecting steps whether said state of said biological sample is quiescence, hyperplasticity or neoplasia.

BRIEF DESCRIPTION OF THE DRAWINGS

The file of this patent includes at least one drawing executed in color.

FIG. 1 illustrates cyclin D1 protein expression in young, old, and transformed fibroblasts.

FIGS. 5A–5C illustrate that cyclin D1 immunoprecipitates contain no detectable histone H1 kinase activity and inhibit cyclin A/cdk kinase activity.

FIGS. 6A–6D illustrate that cyclin D1 inhibits the ability of cdk2 to induce morphological changes.

FIGS. 7A–7D illustrate that microinjected cells express cdk2 and co-injected cyclins simultaneously.

DETAILED DESCRIPTION OF THE INVENTION

Figure 2A:
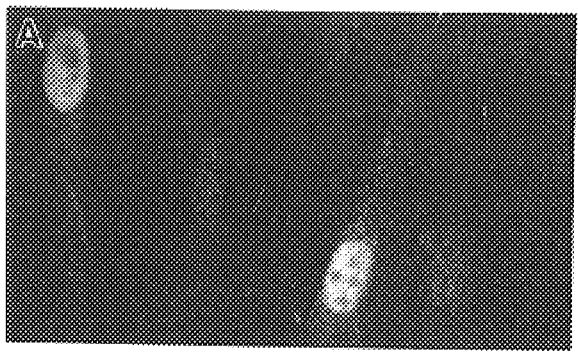
FIGS. 2A–2D illustrate that cells expressing high levels of cyclin D1 do not enter into DNA synthesis.
Figure 2B:
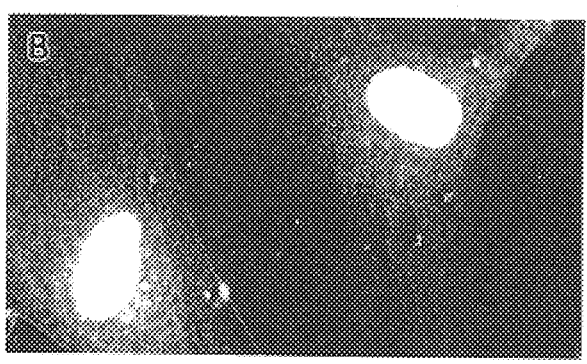
Figure 2C:
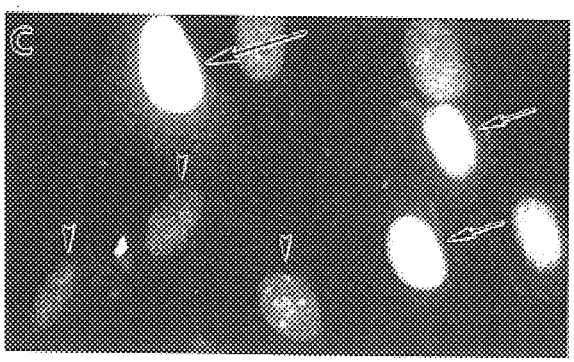
Figure 2D:
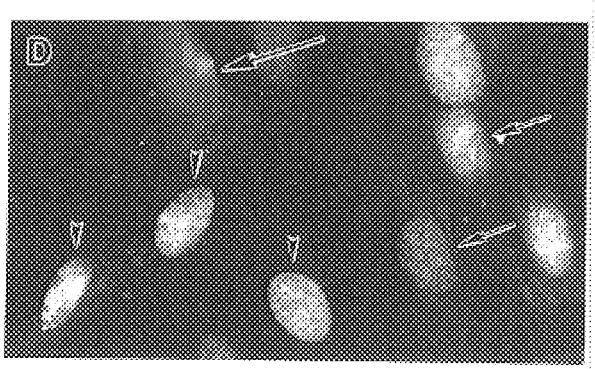

The invention described herein relates to the unexpected discovery that cyclin D1 is a negative regulator of cdk2 kinase activity. Cyclin D1 has been found to complex with cdk2. The cyclin D1-cdk2 complex is not active. Without being bound to any theory, if this interaction with cyclin D1 prevents the cdk2 in a cell from complexing with other cyclins, this would block cell proliferation and growth, since cdk2, in conjunction with the other cyclins, is required for growth. We have found that senescent cells express large amounts of the cyclin D1 protein, indicating that cyclin D1 plays a negative role in cell proliferation.

Definitions

As used herein, the following terms have the following meanings:

"Agent" means an active force or substance capable of producing an effect.

"Antibody" means a molecule that binds to a known antigen.

"Antisense" and "Antisense nucleotides" means DNA or RNA constructs which block the expression of the naturally-occurring gene product. For example, in the present invention, use of a DNA construct that produces cyclin D1 antisense RNA blocks the expression of cyclin D1 by destroying or inactivating cyclin D1 mRNA.

"Biological sample" means a sample of mammalian cells. These cells may be part of a tissue or organ sample obtained, for example, by biopsy, or they may be individual cells, for example, blood cells or cells grown in tissue culture.

"Cancerous Cell" means a cell in or from a neoplasm.

"Cell cycle" means the cyclic biochemical and structural events occurring during growth of cells. The cycle is divided into periods called : $G_0$, $Gap_1$, ($G_1$), DNA synthesis ($S_1$), $GAP_2$ ($G_2$), and mitosis (M).

"Cell division" means mitosis, i.e., the usual process of cell reproduction.

"Code", when used with reference to a nucleotide's relation to a protein, means the system whereby particular combinations of adjacent nucleotides control the insertion of particular amino acids in equivalent places in a protein molecule.

"Cyclin" means one of the proteins which actively regulate cell division. "Cyclin D1 " means one of the D-type cyclins which are encoded by genes shown to be able to replace a CLN-type gene essential for cell cycle start in yeast, which complement a deficiency of a protein essential for cell-cycle start and which, on the basis of protein structure has about 295 amino residues and a molecular weight of about 33, 670 daltons. Cyclin D1 is also known as pradi, cyl1 or CCND1.

"Cyclin-protein kinase complex" means the complex formed when a cyclin associates with a cyclin dependent kinase. Such complexes may be active in phosphorylating proteins and may or may not contain additional protein species.

"Expression" means the production of a protein or nucleotide in the cell.

"Growth" means progression through the cell cycle with the result that two daughter cells are formed from each mother cell. "Actively growing" means that state wherein cells exhibit growth and cell division.

"Hyperplasticity" means an increase in cell number, excluding tumor formation.

"Label" means to incorporate into a compound a substance that is readily detected. Such substances include radioactive substances and fluorescent dyes, for example.

"Mammalian cell" means a cell in or from a mammal, either in a tissue or organ or in tissue culture.

"Neoplasia" means the process resulting in the formation and growth of an abnormal tissue that grows by cellular proliferation more rapidly than normal, and continues to grow after the stimuli that initiated the new growth cease.

"Normal cell" means a non-cancerous cell.

"Proliferating Cell Nuclear Antigen" or "PCNA" means the δ-subunit of DNA polymerase whose expression is tightly controlled during the cell cycle and is strongly and positively correlated with cell growth. PCNA has been shown to associate with cyclin D1.

"Proliferation" means growth and reproduction, i.e., division of cells.

"Protein kinase" means an enzyme catalyzing the phosphorylation of proteins.

"Quiescence" means that part of the cell cycle where the cell is at rest or inactive with respect to proliferation.

"Visualization" means to examine visually, using either the naked eye or microscopic techniques.

Based largely on the observations that some tumor cells show amplification (extra copies) of the cyclin D1 gene and that exogenous human cyclin D1 can restore the ability of yeast mutants deficient in positively-acting CLNS (G1 cyclins) to grow, most researchers have proposed that cyclin D1 acts as a positive regulator of cell growth, sometime during the G1 phase of the cell cycle (38, 39). We have found that this cyclin instead acts as a negative regulator of growth, most likely through interaction with, and inhibition of cyclin-dependent kinases (cdk's). Using needle microinjection and standard transfection techniques, we have direct data which show that this cyclin plays a negative role in growth. Thus, we have found that the endogenous human cyclin D1 gene can be used to control cell growth in a variety of novel ways.

We found that the propensity to enter $G_0$ is proportional to cellular levels of cyclin D1. Cell lines established from tumor cells often lack the ability to enter a quiescent ($G_0$) state, whereas normal human diploid fibroblasts (HDF's) retain this ability and HDF's at the end of their in vitro lifespan (senescent cells) lack the ability to enter the cell cycle in response to normally mitogenic stimuli (24–26). As shown in FIG. 1, immunoprecipitations of [$^{35}$S]-methionine-labelled proteins with α-cyclin D1 antibodies (23) showed that old cells contained higher levels of cyclin D1 than young cells, which themselves expressed more of this cyclin than transformed fibroblasts.

As a measure of the ability of each cell line to enter a state of quiescence in response to serum deprivation, young, old and transformed WI-38 fibroblasts in a logarithmic growth phase were labelled with [$^3$H]-thymidine for 24 hours in the absence and presence of 10% serum. The ability to enter quiescence (quiescence index, QI) was scored as the percentage of cells that did not incorporate [$^3$H]-thymidine (as judged by emulsion autoradiography) over a 24 hour time period when grown in complete medium, divided by the percentage of cells incorporating [$^3$H]-thymidine during the same period when grown in the absence of serum. Results of this assay are shown in Table 1. By this criterion, old fibroblasts entered quiescence most readily (QI=2.1), followed by young (QI=1.7) and transformed cells (QI=1.3). Thus, QI, a measure of the propensity of cells to arrest within the cell cycle (presumably by entry into a state of quiescence) is directly proportional to the cellular levels of cyclin D1 detected by immunoprecipitation.

High levels of cyclin D1 expression correlated with an inability of individual cells to enter DNA synthesis. Young and old fibroblasts deprived of serum for 48 h were refed with medium containing 10% serum and 0.1 μg/ml of bromodeoxyuridine (BrdU), and were incubated for 24 h prior to fixation. Upon staining with affinity-purified cyclin D1 antibodies, young fibroblasts (FIG. 2, panel A) showed variable levels of staining that were generally several fold less intense than staining seen in near senescent cells (panel B). In addition, when both cyclin D1 expression and BrdU incorporation were examined in low passage cultures, the few cells seen that expressed high levels of cyclin D1 were in all cases BrdU-negative (identified by the large arrow in panels C and D). Cells with low levels of cyclin D1 had incorporated high amounts of BrdU (arrowheads in panels C and D) and cells with intermediate levels of cyclin D1 had incorporated lower amounts of BrdU (small arrows).

When examined by similar methods, old cell cultures contained a much larger proportion of cells that were unable to incorporate Brdu and that also showed strong cyclin D1 staining similar to cells shown in panel B. This confirmed that old, near senescent fibroblasts expressed higher levels of cyclin D1 than their young syngeneic counterparts and indicated that cells expressing high levels of cyclin D1 failed to enter S phase in response to mitogen stimulation.

Expression of cyclin D1 protein was down-regulated in response to stimulation by mitogens. The results shown in FIGS. 1 and 2 suggested a negative correlation between cyclin D1 protein expression and cell growth, but previous reports have indicated that cyclin D1 mRNA expression is induced following stimulation of cells with mitogenic agents (17, 27, 38, 39). We performed a time course experiment in which young and old cells rendered quiescent by serum deprivation for 48 hours were pulsed with [$^{35}$S]-methionine in 6 hour intervals before, or after, the addition of serum.

Figure 3A:
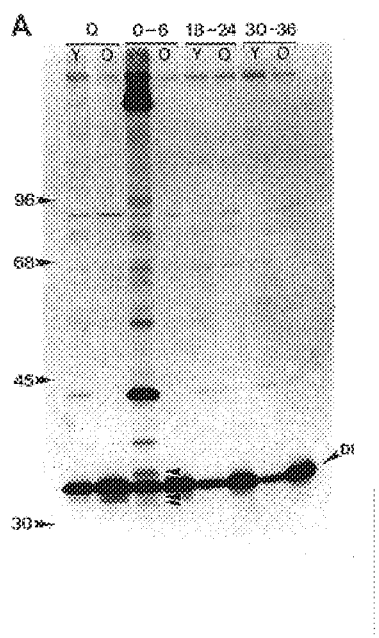
FIGS. 3A–3D illustrate the half life, expression patterns, and protein associations of cyclin D1 protein in young and old fibroblasts.

FIG. 3A shows that at all time points, old fibroblasts expressed higher amounts of cyclin D1 that young cells. Additionally, the amount of D1 expressed by young cells that were capable of serum-induced growth (in these cells DNA synthesis begins 16–18 hours after serum addition under these conditions) progressively decreased as cells traversed the cell cycle.

Figure 3B:
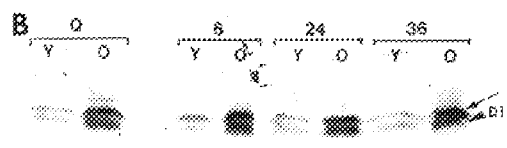

To determine if the band intensities seen in immunoprecipitates reflected accurately the cellular levels of cyclin D1, Western blot analyses of lysates from young and old cells harvested at the same time points shown in FIG. 3A were performed. As shown in FIG. 3B, two bands of slightly different mobility were recognized by the cyclin D1 antibody in this assay compared with the single $^{35}$S-labelled band detected in immunoprecipitates and in Western blots of cyclin D1 immunoprecipitates (12). Both bands were recognized specifically by the cyclin D1 antibody, but not with three different control antibodies. However, preclearing of cell lysates with cyclin D1 antibodies prior to using lysates in Western Blot assays more efficiently eliminated the faster migrating band. This suggested that the slower migrating form, which may correspond to phosphorylated cyclin D1 (19), is less readily recognized under non-denaturing conditions by the cyclin D1 antibody used in this study.

The relative intensities of both bands in old, as compared to young, cells were very similar to results obtained for cyclin D1 by immunoprecipitation assays.

We also noted that immunoprecipitates from old cells contained larger amounts of a minor band migrating ahead of cyclin D1 (ca. 33 kDa; FIG. 3A) that likely corresponds to cyclin-dependent kinases. Additional bands were also recovered from lysates of young cells during the first 6 hours following stimulation which, by similar criteria, correspond to proliferating cell nuclear antigen (PCNA; ca. 36 kDa) and previously seen but uncharacterized proteins (23). We analyzed expression of this cyclin by Northern blot analysis and also found increased levels of cyclin D1 mRNA expression following serum-stimulation of quiescent fibroblasts. It thus seems that cyclin D1 mRNA is subject to a post-transcriptional regulatory mechanism that, at present, remains uncharacterized.

Figure 3C:
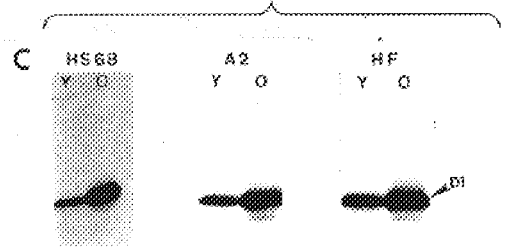
Figure 3D:
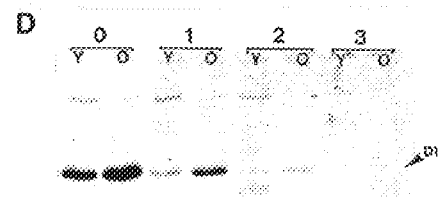

To establish if elevated cyclin D1 protein expression was seen reproducibly in cells as they neared replicative senescence we repeated the experiment described in FIG. 1 on young and old cells from three independent HDF strains. In all cases old fibroblasts expressed considerably higher levels of cyclin D1 than did their young, syngeneic counterparts (FIG. 3C) by factors of three to five-fold (3.1 (HF), 4.2 (A2) and 4.8 (Hs68)). Since it was also possible that our recovery of different amounts of cyclin D1 from young and old fibroblasts was due to increased stability of the cyclin protein in old cells we performed the pulse chase experiment shown in FIG. 3D in which cells were labelled for 1 hour with [$^{35}$S]-methionine and chased with unlabelled medium for increasing 1 hour periods. We estimate that the half lives of the protein in young and old cells are quite similar and short, being approximately 28 and 25 minutes, respectively, in agreement with previous reports (28). These results demonstrated by three independent criteria that cyclin D1 is expressed in near senescent cells at levels several-fold higher than in young, proliferation-competent human diploid fibroblasts.

We found that larger proportions of cdk2 associate with cyclin D1 as cells approach senescence. Previous reports have indicated that cyclin D1 formed complexes with cyclin-dependent kinases in vivo (23, 28). To determine if cyclin D1 interacted similarly with cdks in cells capable or incapable of growth in response to stimulation with mitogens, immunoprecipitations were performed under non-denaturing conditions on [35S]-methionine-labelled lysates from young and old fibroblasts growing asynchronously. Excess amounts of α-p34$^{cdc2}$, α-p33$^{cdk2}$, or α-cyclin D1 antibodies that have been characterized previously (2, 11, 23) were used in all cases.

Figure 4A:
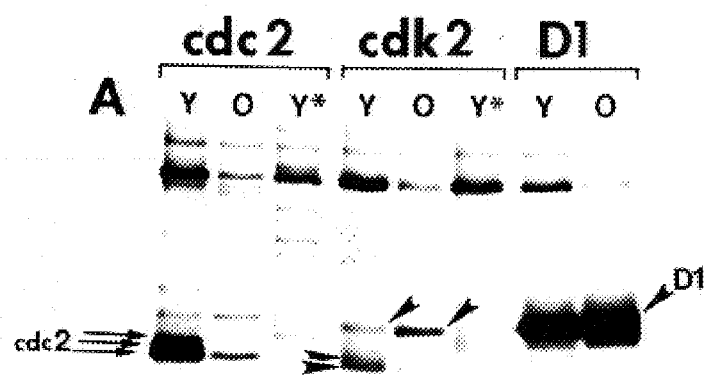
FIGS. 4A and 4B illustrate the decrease of cdk2 synthesis and the increased association of cdk2 with cyclin D1 as fibroblasts age.

As shown in FIG. 4A, expression of the 3 known isoforms of p34$^{cdc2}$ (indicated by horizontal arrows) are markedly reduced in old, as compared to young proliferation-competent cells, in agreement with previous reports (29, 30). Similar results were obtained upon immunoprecipitating with antibodies raised and affinity-purified against the p33$^{cdk2}$ kinase (horizontal arrowheads in FIG. 4A), indicating that the expression of this kinase is also reduced in aging fibroblasts. As controls for specificity, the lanes marked Y* show that preincubation of the antibodies with bacterially expressed cognate (p34$^{cdc2}$ or a GST-p33$^{cdk2}$ fusion) proteins efficiently blocked precipitation of these kinases from young cell lysates. In contrast to the decreased levels of expression of these two cdks, more cyclin D1 was again recovered from extracts prepared from old fibroblasts (FIG. 4A). This increase was also reflected by increased amounts in old cells, of a protein identical in $M_1$ to cyclin D1 that was recovered in complex with p33$^{cdk2}$ when immunoprecipitating with α-p33$^{cdk2}$ antibodies (indicated by oblique arrowheads).

Figure 4B:
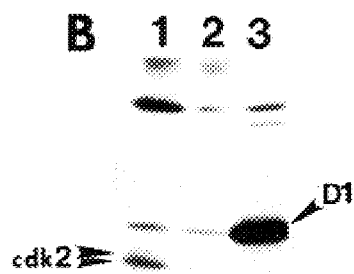

To determine if the protein band recovered in α-p33$^{cdk2}$ immunoprecipitations contained cyclin D1, a lysate from young HDF's was preincubated with cyclin D1 antibodies and proteins recognized by this antibody were removed by the addition of protein A-Sepharose. As shown in FIG. 4B, when lysate precleared with cyclin D1 antibodies (lane 3) was immunoprecipitated with α-p33$^{cdk2}$ antibodies (lane 2), considerably less p33$^{cdk2}$ was recovered (compare lane 1, which was immunoprecipitated with α-p33$^{cdk2}$ only, with lane 2) indicating that only a fraction of the protein migrating with an $M_r$ of 33 kDa, was complexed with cyclin D1.

This observation was in agreement with previous reports demonstrating a physical association between cyclin D1 and cyclin dependent kinases (23, 28). The fact that we observed a greater signal intensity for cyclin D1 than for p33$^{cdk2}$ when immunoprecipitating lysates from old cells with α-p33$^{cdk2}$ antibodies was likely due to the high turnover rate of the cyclin D1 protein. Thus, in addition to lower levels of p33$^{cdk2}$ being expressed in old cells, these data indicate that a larger percentage of the kinase that is expressed is held in a complex with cyclin D1. In contrast, similar p33$^{cdk2}$:cyclin A ratios were seen when immunoprecipitating lysates from young and old fibroblasts with α-cyclin A antibodies. This may reflect the fact that in contrast to cyclin D1, cyclin A is expressed at very low levels in old fibroblasts (29, 30).

p33$^{cdk2}$ is also known to associate with at least two other cyclins (cyclins A and E; 4, 11, 15, 16) in complexes that have readily measurable kinase activities. Because kinase activity has not been detected in cyclin D1/p33$^{cdk2}$ complexes, these results suggested that cyclin D1 may sequester cdk2 and possibly other kinases (cdk4, cdk5) in an inactive state, resulting in a selective loss of activity in senescent cells.

Cyclin D1 protein complexes showed no intrinsic histone H1 kinase activity and inhibited cyclin A/cdk2 kinase activity. To address the possibility that cyclin D1 negatively regulated kinase activity we performed a series of immunoprecipitations using α-cyclin A or α-cyclin D1 antibodies and used the products recovered on protein A-Sepharose beads in kinase assays using purified histone H1 as substrate. While cyclin A antibodies recovered proteins with high levels of kinase activity, such activity was not seen in control pre-immune or in cyclin D1 immunoprecipitates (FIG. 5A) in agreement with other reports (19). Additionally, lysates from old cells contained barely detectable levels of cyclin A-associated kinase activity (compare lanes 3 and 4), which likely reflect the lack of expression of this kinase in senescent fibroblasts (29, 30).

To determine if cyclin D1 could affect the kinase activity of cyclin A immunoprecipitates, equal volumes of control (pre-immune sera), cyclin A, or cyclin D1 immunoprecipitates from young or old cell lysates were added to cyclin A immunoprecipitated from young cells. Protein A-Sepharose beads from these reactions were mixed and incubated at 37° C. for 20 minutes prior to the addition of $[(\gamma-^{32}P)]$-ATP and histone H1 substrate. As shown in FIG. 5B, addition of immunoprecipitates using control or α-cyclin A antibodies did not affect the histone H1 kinase activity immunoprecipitated from young fibroblasts (compare lane 3 of FIG. 5A with lanes 2 and 3 of FIG. 5B) indicating that immunoprecipitation complexes from lysates did not contain non-specific inhibitors of histone H1 kinase activity. In contrast, cyclin D1 immunoprecipitated from young (FIG. 5B, lane 1) or from old fibroblasts (FIG. 5B, lane 4) markedly inhibited the kinase activity associated with cyclin A immunoprecipitates. Moreover, cyclin D1 immunoprecipitates from old cell lysates inhibited cyclin A/cdk kinase activity more efficiently that similar immunoprecipitates from young cells, most likely reflecting the increased cellular levels of cyclin D1 in old fibroblasts.

To define further the specificity of cyclin D1 inhibition of kinase activity, an additional set of kinase mixing experiments was done using antibodies that recognize the cdc2 kinase. This kinase does not appear to associate with cyclin D1 (FIG. 4A) and the antibody does not block kinase activity of immunoprecipitates (2). Lanes 3 and 4 of FIG. 5C show the histone H1 kinase activity recovered by immunoprecipitation of young cell lysates with cdc2 and cyclin A antibodies, respectively. While mixing of cyclin D1 immunoprecipitates from old cells again inhibited the cyclin A kinase activity precipitated from young cells (compare lanes 4 and 9), cyclin D1 immunoprecipitates did not affect cdc2 kinase activity (compare lanes 3 and 5). Additionally, minimal effects on activity were seen when cyclin A immunoprecipitations from young cells were mixed with protein A-Sepharose beads incubated in old cell extract (lane 6), with control antibodies incubated in old cell lysates and recovered on protein A-Sepharose beads (lane 7), or with cyclin D1 antibodies recovered from lysis buffer on protein A-Sepharose beads (lane 8). Thus, inhibition of cyclin A-associated kinase activity by cyclin D1 immunoprecipitates is not due to nonspecific factors in young or old cell lysates, nor is it due to the cyclin D1 antibody itself, but depends upon the amount of cyclin D1 added to cyclin A immunoprecipitates (FIG. 5B, lanes 1 and 4). These results show that under these conditions, cyclin D1 isolated from normal primary diploid fibroblasts competes for kinase catalytic subunits with cyclin A, effectively blocking cyclin A/cdk2 activity.

To determine if such an inhibitory effect upon kinase activity could be observed directly in vivo, expression constructs encoding $p33^{cdk2}$ and cyclins A, D1 and E were microinjected into fibroblasts both singly and in paired combinations, and their effects upon cell morphology were determined. Injected cells were identified by staining with α-cdk2 antibodies. As shown previously for the injection of other kinases (31, 32), the effect of increased cdk2 activity within cells was readily observed as a loss of cytoskeletal integrity (FIG. 6A). Co-expression of cyclins A (FIG. 6, panel B) and E (FIG. 6, panel C) augmented the kinase activity (as estimated by the degree of cytoskeletal collapse) seen with cdk2 alone, suggesting that these cyclins were limiting when cdk2 alone was overexpressed. Conversely, co-expression of cyclin D1 with cdk2 (FIG. 6, panel D) blocked the cytoskeletal collapse seen with cdk2 alone, or with cdk2 co-injected with either cyclin A or E, indicating that cyclin D1 inhibited kinase activity. Expression levels of the cyclin constructs used here have been characterized previously (33). However, since the effect that we observed upon cell morphology may have been due, in part, to variable levels of cyclin expression, we repeated the coinjection experiments described above and visualized the expression of cdk2 and of the co-injected cyclins within individual cells. As shown in FIG. 7, cyclins A (panel C) and D1 (panel D) were expressed to similar levels despite pronounced differences in cell morphology, supporting the idea that differences in morphology were due to effects of these cyclins upon cdk2 activity in this in vivo model.

Figure 9A:
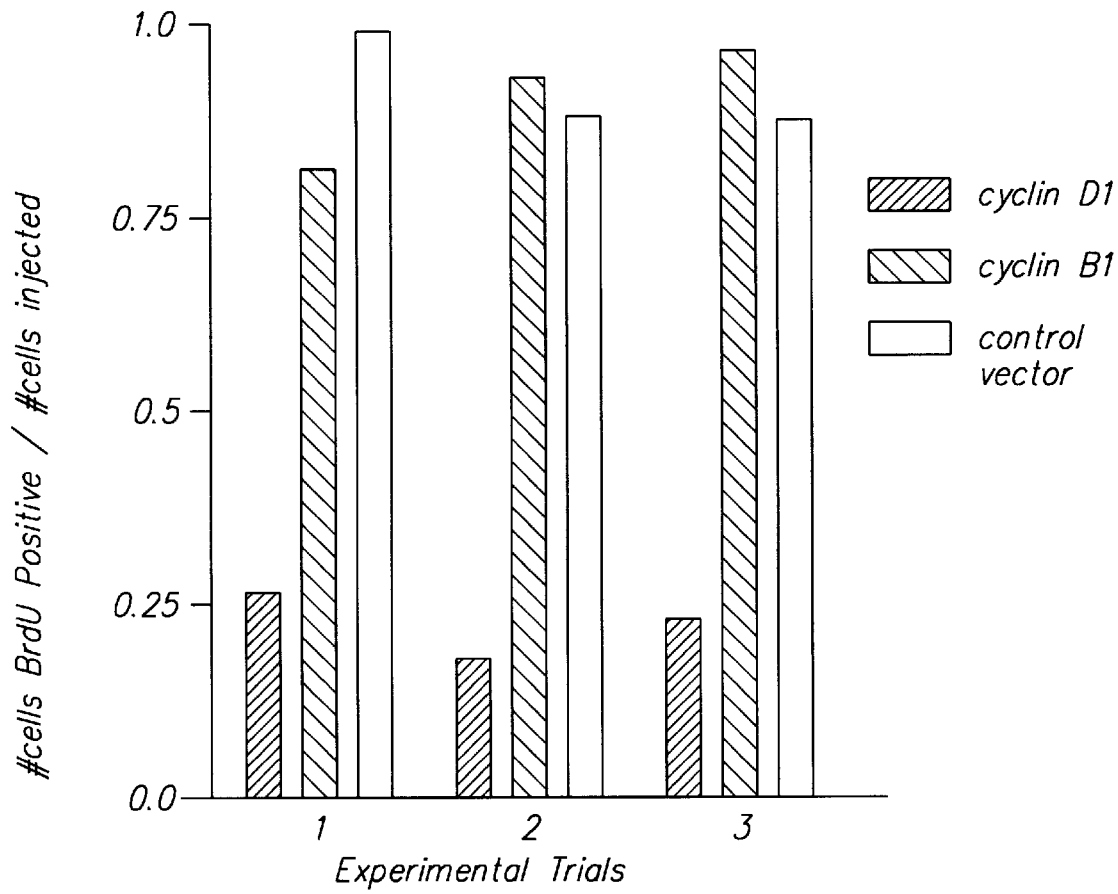
FIGS. 9A and 9B illustrate that elevated levels of cyclin D1 block cell growth.
Figure 9B:
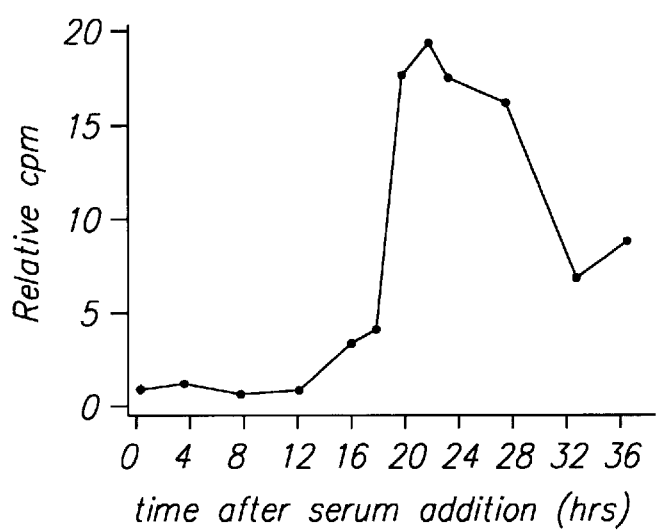

As seen in FIG. 9, needle microinjection of cyclin D1 expression constructs into Hs68 fibroblasts was performed to test the effect of cyclin D1 overexpression on the ability of these cells to enter into DNA synthesis (as a measure of cell growth). The data show that elevated levels of cyclin D1 blocked cell growth.

Figure 8:
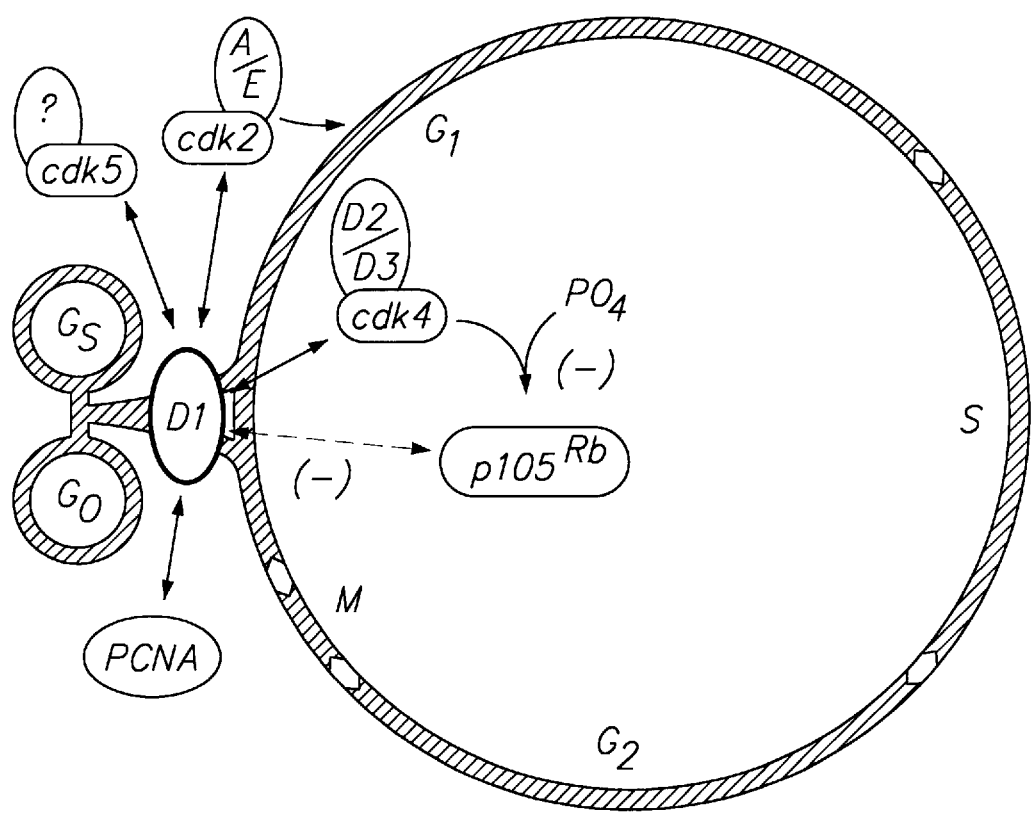
FIG. 8 illustrates a possible role for cyclin D1 in regulating traverse of the G1–G0 boundary.

Our results indicate that cyclin D1 serves a negative role in regulating the activity of cdk2. Since we have shown recently that the activity of cdk2, most likely in a complex with cyclin E, is required for entry into S phase (11), cyclin D1 may serve to sequester this, and possibly other kinase catalytic subunits in response to decreased levels of extracellular mitogens. This sequestration could then have the effect of promoting the exit of cells from the cell cycle into a state of quiescence as diagrammed in FIG. 8. Consistent with this proposal, we have found a direct correlation between cyclin D1 levels and the propensity of cells to enter a state of quiescence in response to mitogen withdrawal. Additionally, we find that actively growing cells synthesize less cyclin D1 protein than quiescent cells and individual cells that express high levels of cyclin D1 do not enter S phase in response to mitogen stimulation. Reports that several myeloid and lymphoid cell lines that typically display rapid growth rates and do not survive mitogen withdrawal by entering a quiescent state are devoid of cyclin D1 expression (18) is also consistent with cyclin D1 playing a role in exit from the cell cycle. In addition to cdk2, cdk4 also associates with cyclins D1 and D3 (23, 28, 35). Since cyclin D3/cdk4 has been reported to phosphorylate $p105^{Rb}$ (28) and would therefore be expected to positively regulate cell growth, sequestration of cdk4 by cyclin D1 into a catalytically inactive complex would lead to underphosphorylated $p105^{Rb}$ and subsequent growth inhibition.

Based largely on the observations that mammalian cyclin D1 can complement conditional G1 yeast mutants (14) and that the cyclin D1 gene is overexpressed in some types of tumors (17, 36 and references therein), a positive role in cell growth for cyclin D1 during G1 has been proposed. Conversely, the observations that the mitotic cyclin B1 can also complement G1 yeast mutants (14), that many transformed cell lines and tumors that show rapid growth lack cyclin D1 expression (18–22), and that high levels of cyclin D1 expression in normal diploid cells is strongly correlated with a lack of growth, suggest a negative role for this cyclin in cell growth. Experiments in which the ability of overexpressed cyclin D1 to affect a $p105^{Rb}$-induced block to cell growth in the highly transformed cell line SAOS-2 suggest in one case, that cyclin D1 has a weak positive effect on cell cycle traverse (36) while others have reported a weak, potentially inhibitory effect on growth as assayed by colony formation (35). These reports do establish, however, that the D-type cyclins can bind to $p105^{Rb}$ with varying avidities when expressed in vitro or when overexpressed in tissue culture cells, suggesting different cellular functions (35, 36). Cyclin D2, and possibly D3 appear to bind to and phosphorylate $p105^{Rb}$ much more efficiently than cyclin D1 and when coexpressed with cyclin D1, cdk4, but not cdk2 was capable of phosphorylating bacterial GST-Rb fusion proteins (35). Indeed, the ability of cyclins A, B1, D2, D3 and E, but not cyclin D1 to positively regulate cdk2 activity when overexpressed in insect cells has led some to speculate recently that cyclin D1 might negatively regulate cdk2 kinase activity (35), a result we found here in normal diploid fibroblasts using in vitro and in vivo assays.

Without being bound to any theory, we propose that cyclin D1 supplies a function necessary for entry into, and exit from the cell cycle. (See FIG. 8.) The state of senescence ($G_s$) is viewed as similar to, but distinct from that of quiescence ($G_0$ for a recent review see reference 26). Here cyclin D1 is envisioned to play a role inthe sequestration of other cell cycle regulatory proteins such as the cdk2 and cdk4 kinases into inactive protein complexes. Thus, cyclin A/cdk2 and cyclin E/cdk2 kinase activity (11, 15, 16) would be negatively regulated by cyclin D1 competing for the catalytic subunit cdk2. In addition, cyclin D1 may also directly or indirectly inhibit the phosphorylation state and/or expression of $p105^{Rb}$ as suggested by others previously (28, 33). Such a dual function in which the cellular levels of cyclin D1 affected the expression of growth-inhibitory genes and the distribution/activity of other cellular polypeptides thereby affecting the ability of cells to enter and to exit $G_0$, would be consistent with the growth states of cells expressing this cyclin at different levels. For example, in senescent cells that are unable to exit "$G_s$", cyclin D1 is expressed at high levels, normal fibroblasts that can enter and exit $G_0$ in response to availability of mitogens show moderate levels and transformed cell lines that do not readily enter $G_0$ express low levels, or in some cases totally lack cyclin D1.

An alternative interpretation of our results regarding kinase activity is that upon association with cyclin D1, cdk2 acquires altered substrate specificity and is therefore unable to phosphorylate efficiently the substrates that our assays were designed to investigate (i.e. histone H1 and cytoskeletal components). The recent report that cyclin D3 in the presence of cdk4 is capable of phosphorylating $p105^{Rb}$ (28, 35, 36) makes this possibility tenable. However in other studies (33), no changes in $p105^{Rb}$ phosphorylation were seen in response to cyclin D1 immunoprecipitate and we have shown that cyclin D1 is capable of inhibiting directly the kinase activity of cyclin A/cdk complexes formed in vivo. Our data support the idea that cyclin D1 serves to regulate the activity of kinase catalytic subunits that are shared among different cyclin molecules. In particular, by negatively regulating the cyclin/cdk activities required for progression through different points of the cell cycle, cyclin D1 may promote or possibly control the transition from active growth into a state of quiescence.

One advantage of the present invention is that there are no existing methods, devices or other means to modify cell growth in this way. Methods using combinations of other genes such as Ras and p53 have been proposed to be used in similar ways for treating different forms of cancer but such studies, although underway, are preliminary. An additional advantage of proposed technology lies in the point of the cell cycle that we believe cyclin D1 exerts its effect. Ras and p53 will effect gene products that are active throughout the cell cycle, and likely serve many different cellular functions. Thus, the cellular effects that one would expect by blocking the expression of Ras and enhancing the expression of p53 are unclear. Since cyclin D1 operates within the cell by affecting entry into, and exit from, the cell cycle, the effect of increasing or decreasing cyclin D1 expression will have predictable consequences upon the target cells whether they have normal diploid or transformed cancerous phenotypes.

The present invention may be used to block the growth of cancer cells by increasing expression of cyclin D1, and to promote the growth of near-senescent cells by lowering (or blocking) the expression of cyclin D1 protein. Blocking the growth of cancer cells is of obvious importance and is limited mainly by our ability to deliver cyclin D1 expression constructs to target tissues. An appropriately driven antisense construct will allow blocking of cyclin D1 expression in mammalian cells. Viral vectors may be used to deliver sense and antisense constructs to target cells in vivo. Such methods are known in the art (41).

Since blocking cyclin D1 expression enables near-senescent cells to undergo additional cell divisions, uses include the promotion of surface wound healing, especially in the elderly, and decreasing the incidence of gastrointestinal infection, especially in the elderly where increased incidence of infection is believed to be due, in part, to the inability of cells of the intestinal epithelium to proliferate sufficiently to maintain integrity of the intestinal wall. It is expected that lipofection techniques may be used to deliver DNA constructs to targets both in vitro and in vivo.

The present invention also has diagnostic use, since we have found that cells that express high levels of cyclin D1 are unable to enter the cell cycle in response to addition of normally mitogenic agents (FIG. 2). Thus, simple immunochemical staining of cells or sections of cells should give an accurate estimate of the portion of cells actively growing (and especially those not growing). Such a test based on the production and use of cyclin D1 antibodies and standard secondary techniques of visualization will be useful in cancer diagnosis. Such a test of cellular quiescence might also be useful to the scientific research community.

Cyclin D1 expression can be detected and/or quantitated and the results used as an indicator of the rate of cell division. High levels of cyclin D1 in the cells of a biological sample will indicate that such cells have a low rate of proliferation. Low levels of cyclin D1 will indicate an abnormally high rate of cell division.

In a diagnostic method of the present invention, cells obtained from an individual or a culture are processed in order to determine the extent to which cyclin D1 is present in cells, in a specific cell type or in a body fluid. This can be determined using known techniques and an antibody specific for cyclin D1. Comparison of results obtained from cells or a body fluid being analyzed with results obtained from an appropriate control (e. g., cells of the same type known to have normal cyclin D1 levels or the same body fluid obtained from an individual known to have normal cyclin D1 levels) is carried out. Decreased cyclin D1 levels are indicative of an increased probability of abnormal cell proliferation or oncogenesis or of the actual occurrence of abnormal proliferation or oncogenesis. Such antibodies to cyclin D1 will generally be detectably labelled (e.g., with a radioactive label, a fluorescent material, biotin or another member of a binding pair or an enzyme).

A method of inhibiting cell division, particularly cell division which would otherwise occur at an abnormally high rate, is also possible. For example, increased cell division is reduced or prevented by introducing into cells a drug or other agent which can increase, directly or indirectly, expression of cyclin D1. In one embodiment cyclin D1 protein is introduced directly. In another embodiment nucleotides coding for cyclin D1 are introduced.

Cell division may be increased by preventing transcription and/or translation of cyclin D1 DNA and/or RNA. This can be carried out by introducing antisense oligonucleotides into cells, in which they hybridize to the cyclin-encoding nucleic acid sequences, preventing their further processing. It is also possible to inhibit expression of cyclin D1 by the addition of agents which degrade cyclin D1. Such agents include a protease or substance which enhances cyclin D1 breakdown into cells. In either case, the effect is indirect in that less cyclin D1 is available than would otherwise be the case.

Antibodies specifically reactive with cyclin D1 can be produced, using known methods. For example, anti-cyclin D1 antisera can be produced by injecting an appropriate host (e.g., rabbits, mice, rats, pigs) with cyclin D1 and withdrawing blood from the host animal after sufficient time for antibodies to have been formed. Monoclonal antibodies can also be produced using known techniques.

A hybridization probe prepared from a segment of nucleotides of cyclin D1-encoding RNA, cyclin D1 cDNA or cyclin D1 genomic DNA may be employed as a means for determining the number of copies of cyclin D1 present in the genomic DNA of a given sample, or the level of cyclin D1 mRNA expressed in cells of such sample.

The following examples are offered to illustrate this invention and are not meant to be construed in any way as limiting the scope of this invention.

EXAMPLES

Example 1

Propensity of young, old and transformed W1-38 cells to exit the cell cycle in response to serum withdrawal.

Parallel cultures of subconfluent young (Y), old (O) or SV40-transformed (Tr) fibroblasts growing on 35 mM culture dishes were refed with medium containing (+Ser) or lacking (-Ser) 10% fetal bovine serum. [$^3$H]-thymidine (1 µCi/ml) was added as a bolus to all cultures and cells were grown for 24 h prior to fixation and analysis by emulsion autoradiography as described (2, 11). Quiescence Index (Q.I.) was calculated by dividing the percentage of labelled nuclei seen in cells grown in the continuous presence of medium containing 10% serum by the percentage of labelled nuclei in cells under conditions of serum withdrawal. (A Q.I. of 1.0 indicates no difference in the tendency of cells to enter S phase in the absence or presence of serum.)

The results, shown in Table 1, indicate that old fibroblasts entered quiescence most readily, followed by young and transformed cells.

TABLE 1

|  |  | Total # examined | # Labelled | % Labelled | OI |
|---|---|---|---|---|---|
| WI-38-Y | +Ser | 160 | 83 | 52 |  |
|  | -Ser | 210 | 65 | 31 | 1.7 |
| WI-38-O | +Ser | 194 | 33 | 17 |  |
|  | -Ser | 206 | 16 | 8 | 2.1 |
| WI-38-Tr | +Ser | 119 | 108 | 91 |  |
|  | -Ser | 243 | 170 | 70 | 1.3 |

Example 2

Cyclin D1 protein expression in young, old and transformed fibroblasts.

To determine if the expression of cyclin D1 was correlated to the ability of cells to enter $G_0$ we compared the levels of cyclin D1 protein in syngeneic proliferation-competent ("young"), near-senescent ("old") and SV40 T antigen-transformed WI-38 cells.

Senescent (60 mean population doublings; MPDs) and proliferation-competent (26 MPD) WI-38 cells (ATCC CCL #75), and SV40-transformed WI-38 fibroblasts (ATCC CCL #75.1, VA13 subline 2RA) were grown in DMEM containing 10% FBS and were subcultured within 3 days of attaining confluence at split ratios of 1:2 to 1:8. Asynchronously growing cells at 75% of confluence were refed with DMEM minus methionine containing 10% FBS and 0.1 mCi/ml of [$^{35}$S]-methionine. Following incubation for 3 h, cells were washed with ice-cold PBS and harvested on ice in RIPA buffer (20 mM Tris-HCl, pH 7.5/100 mM NaCl/5 mM KCl/1 mM EDTA/0.25% deoxycholate/0.25% Nonidet P-40/0.25% Tween 20) under non-denaturing conditions. Harvesting, immunoprecipitations, gel electrophoresis and visualization of resolved immunoprecipitation products by fluorography were done as described (34).

Equal [$^{35}$S]-methionine counts from young (Y), old (O) and SV40-transformed (T) human fibroblast cell lysates were immunoprecipitated with excess cyclin D1 antibody (23) under non-denaturing conditions. Results are shown in FIG. 1. The large arrow identifies cyclin D1 and the small arrows indicate polypeptide species that migrate with $M_r$s similar to cyclin-dependent kinases. Lane M shows relative molecular mass markers.

These results show that old cells contained higher levels of labelled cyclin D1 than young cells. Transformed fibroblasts expressed less cyclin D1 than young cells.

Example 3

Expression levels of cyclin D1.

Fibroblasts grown on glass coverslips were fixed 24 h after refeeding with complete medium contain 0.1 µg/ml BrdU as described (2), followed by incubation in 3N HCl for 10 min at 25° C. Cells were neutralized in 0.1M borate buffer (pH 8.0) for 2 minutes and stained with rabbit α-cyclin D1, sheep α-rabbit IgG-biotin and Strepavidin-Texas Red to visualize cyclin D1 expression and concurrently with mouse α-BrdU and sheep α-mouse IgG-Fluorescein to detect incorporation of BrdU as a measure of DNA synthesis. Exposure and printing conditions for cells stained with cyclin D1 antibodies were identical to allow direct comparison of fluorescence intensities. Results are shown in FIG. 2.

Expression levels of cyclin D1 were estimated in young (panels A and C) and old (panel B) fibroblasts by indirect immunofluorescence. Staining of young cell cultures for cyclin D1 expression (panel C) and incorporation of BrdU (panel D) indicated that cells expressing high levels of cyclin D1 failed to synthesize DNA as estimated by BrdU staining (large arrow) while the majority of cells expressing low levels of cyclin D1 had entered S phase (arrowheads). A total of 120 cells showing high levels of cyclin D1 were examined for incorporation of BrdU. In 92% (110/120) of these cells BrdU immunofluorescence was not detected.

Example 4

Half life, expression patterns and protein associations of cyclin D1 protein in young and old fibroblasts.

Subconfluent young (Y) and old (O) fibroblasts deprived of serum for 48 h were refed with medium containing 0.1 mCi/ml of [$^{35}$S]-methionine for varying durations and at different times following stimulation. For panel A, equal numbers of [$^{35}$S]-cpm from young and old cells at each time window corresponding to early G1 (0–6), early S (18–24) and late G2/M (30–36) were immunoprecipitated with excess cyclin D1 antibodies under non-denaturing conditions to preserve protein-protein interactions. The relative intensities of signals corresponding to cyclin D1 from different fibroblast strains and for the determination of half life were estimated by scanning autoradiograms using a Hewlett Packard Scan-Jet II and data were used to calculate cyclin half lives according to the formula $T_{1/2}=0.3\ t/(\log D_1/D_2)$. Results are shown in FIG. 3.

Panel A: Cells were labelled for 6 h prior to serum addition when quiescent (Q), or for the 6 h periods indicated following serum-stimulation of quiescent cells. The relative mobilities of molecular mass standards are indicated on the left side of the panel and association of protein bands believed to represent cdks and PCNA with cyclin D1 are indicated by the horizontal lower and upper arrowheads, respectively. The identities of other protein bands associating with cyclin D1 during the 0–6 h time point are unknown.

Panel B: Cyclin D1 levels were measured in lysates prepared from young and old cells at times corresponding to those shown in FIG. 3A (quiescent cells, or cells at 6, 24 or 36 h after serum addition) by Western bolt analysis using cyclin D1 antibodies and alkaline peroxidase -conjugated secondary antibody.

Panel C: Young and old Hs68 (36 and 82 MPD), A2 (24 and 66 MPD) and HF (34 and 72 MPD) primary diploid fibroblasts were labelled and immunoprecipitated as described above.

Panel D: Subconfluent young and old HDFs labelled with [$^{35}$S]-methionine for 1 hour were harvested immediately after labelling (O) or were "chased" by refeeding with cold medium for 1, 2 or 3 hours prior to harvesting. Following immunoprecipitation, electrophoresis and autoradiography, bands corresponding to cyclin D1 were quantitated as described above.

These results show that old cells synthesized higher amounts of cyclin D1 at all time points than young cells.

Example 5

Decreased expression of cdk2 and increased cdk2 association with cyclin D1.

FIG. 4, Panel A

Horizontal arrows indicate the 3 isoforms of p34$^{cdc2}$ recognized by α-cdc2 antibodies in young cells, only one of which is detected in lysates from old cells. Horizontal arrowheads indicate the 2 forms of p33$^{cdk2}$ detected in young cells. Oblique arrowheads identify cyclin D1 that is overexposed in this panel to allow the visualization of cdks. Results of preincubating α-p34$^{cdc2}$ or α-p33$^{cdk2}$ antibodies with bacterially produced cognate proteins prior to immunoprecipitation of lysates prepared from young cells are shown in lanes Y. The major isoform of p33$^{cdk2}$ that is recognized by α-p33$^{cdk2}$ antibodies in lysates from young cell extracts migrates slightly ahead of p34$^{cdk2}$ and is barely detectable in lysates from old cells. Immunoprecipitations of lysates prepared from asynchronously growing young and old cells with α-cyclin D1 antibodies are shown in lanes D1. Bands recovered with this antibody co-migrated with the approximately 35 kDa band co-precipitated with α-cdk2 antibodies (indicated by oblique arrowheads).

FIG. 4, Panel B

Two aliquots of total [$^{35}$S]-methionine-labelled cell lysate from young asynchronously growing Hs68 cells were immunoprecipitated with α-p33$^{cdk2}$ (lane 1) or with α-cyclin D1 (lane 3). Following recovery of antibody-antigen complexes on protein A-Sepharose, the lysate previously precipitated with α-cyclin D1 was then reprecipitated with α-p33$^{cdk2}$ (lane 2). Re-precipitation yielded less recoverable p33$^{cdk2}$ than obtained from fresh lysates, whereas preclearing lysates with cyclin D1 antibodies did not reduce appreciably the signal obtained with α-p34$^{cdc2}$ antibodies (data not shown).

All manipulations were done at 4° C. to preserve protein-protein interactions.

These results showed that cdk2 activity decreased by two mechanisms as fibroblasts aged. These mechanisms were decreased expression of cdk2 and increased cdk2 association with cyclin D1.

Example 6

Histone H1 kinase activity of cyclin D1 immunoprecipitates and their inhibition of cyclin A/cdk kinase activity in vitro.

Kinase assays were done as described (11). Results are shown in FIG. 5.

Panel A: Immunoprecipitate-associated Histone H1 kinase activity from young (Y) and old (O) HDFs when immunoprecipitating with control (lanes 1 and 2), cyclin A (lanes 3 and 4) or cyclin D1 (lanes 5 and 6) antibodies.

Panel B: Aliquots of equal volume and protein concentration from the lysates prepared from young and old cells that were used in panel A were immunoprecipitated with α-cyclin A (young cell lysates), or with pre-immune, cyclin A or cyclin D1 antibodies (old cell lysates). Following recovery of antibody-antigen complexes with protein A-Sepharose, pre-immune (lane 2), α-cyclin A (lane 3) or α-cyclin D1 (lane 4) immunoprecipitates from old cells were mixed and incubated 20 minutes with α-cyclin A immunoprecipitates prior to performing kinase assays. Lane 1 shows the effect of adding a cyclin D1 immunoprecipitate from young cell extracts to a cyclin A immunoprecipitate from young cell extracts.

Panel C: Lanes 1 to 4 show the kinase activity associated with young cell lysate immunoprecipitates using buffer (no antibodies, lane 1), preimmune control antibodies (lane 2), the p34$^{cdc2}$ antibodies used in FIG. 4 (lane 3) and cyclin A antibodies (lane 4). Lanes 5 to 9 show the kinase activities obtained as in panel B, after mixing the following immunoprecipitates: lane 5, a cdc2 immunoprecipitate of young cells with a cyclin D1 immunoprecipitated from old cells (cdc2-Y+cycD1–0); lane 6 cycA-Y+protein A-Sepharose beads-0; lane 7, cycA-Y+control antibodies-0; lane 8, cycA-Y+cycD1-no extract; lane 9, cycA-Y+cycD1-0.

These results show that cyclin D1 immunoprecipitates contain no detectable histone H1 kinase activity and inhibit cyclin A/cdk kinase activity in vitro.

Example 7

Effect of cyclins A, E, and D1 on the ability of cdk2 to induce morphological changes in vivo.

Microinjection, fixation, staining and photography were done as described (34). Results are shown in FIG. 6.

HDFs injected with 0.05 μg/μl of a cytomegalovirus-driven cdk2 expression construct (panel A; 11), or with mixtures containing 0.05 μg/μl of this construct and 0.2 μg/μl of similar plasmids encoding cyclin A (panel B; 33), cyclin E (panel C; 33) or cyclin D1 (panel D; 33) were incubated 16 hours following injection, and were then fixed, stained and visualized by indirect immunofluorescence using α-cdk2 antibodies to detect cells expressing cdk2. Results obtained were also seen using Hs68 (38) primary diploid fibroblasts. The bar indicates 20 μM.

These results showed that cyclin D1 inhibited the kinase activity of cdk2.

Example 8

Expression of cdk2 and cyclins in microinjected cells.

Cells injected as described in FIG. 6 were stained for the expression of cdk2 with mouse α-cdk2 antiserum and were visualized using goat α-mouse IgG-fluorescein. Cyclin A and D over-expression was detected using rabbit antibodies directed against these cyclins followed by goat α-rabbit IgG-biotin and strepavidin-Texas Red.

FIG. 7, Panels A and B show cells co-injected with, and stained for, the expression of cdk2 and cyclin A, respectively. Panels C and D are of cells co-injected with, and stained for, the expression of cdk2 and cyclin D1, respectively.

These results show that microinjected cells expressed cdk2 and co-injected cyclins simultaneously.

Example 9

Effect of elevated levels of cyclin D1 on cell growth.

Hs68 fibroblasts were injected with an empty expression construct (control) or with constructs encoding cyclin B1 or cyclin D1. Cells were incubated 48 hours in the absence of serum to promote entry into a state of quiescence. Cells were refed with complete medium containing serum and BrdU, incubated for 48 hours and were fixed and assayed by indirect immunofluorescence and visual inspection for the expression of cyclin D1 and for the incorporation of BrdU (as a measure of DNA synthesis). Results are given in FIG. 9 for three separate experiments in which 60–110 cells were injected and examined. Panel B shows the time course of entry into DNA synthesis following serum deprivation and subsequent refeeding for Hs68 primary diploid fibroblasts.

These results show that elevated levels of cyclin D1 blocked cell growth.

Example 10

Transfection of cyclin D1 expression constructs to test the effect of chronic elevation of cyclin D1 on cell growth.

Transfection using the technique of electroporation to introduce cyclin D1 expression constructs has been conducted. Cells were selected with the neomycin analog G418. These assays of colony formation have shown that the introduction of the parental construct that confers resistance to G418 allowed cells that take up the plasmid to establish large colonies in this assay, that cells transfected with the same construct in addition to the mitotic cyclin B1 likewise established similar size colonies and numbers of colonies, and that the parental construct also encoding cyclin D1 was also able to establish colonies. However, colonies thus selected did not express high levels of cyclin D1, but only conferred resistance to G418, due to the growth inhibitory effect of the cyclin D1 gene product.

Example 11

Acute microinjection and chronic transfection experiments using a construct expressing antisense RNA of the cyclin D1 gene.

These experiments will show that blocking the expression of the gene product cyclin D1 promotes cell growth. In order to block cyclin D1 expression we will synthesize a DNA construct that produces cyclin D1 antisense RNA under the control of the cytomegalovirus promoter. Use of this promoter will allow constitutive high level expression of the D1 antisense RNA such that cyclin D1 mRNA will be either destroyed within the cell or inactivated in such a way as to prevent cyclin D1 protein synthesis. We will also place both the sense and antisense orientations of the cyclin D1 gene under the control of the steroid-inducible mouse mammary tumor virus (MMTV) promoter which should make high level expression of these constructs dependent upon the presence of steroid hormone. Such constructs may prove especially useful in blocking the growth of cells such as many found in cases of breast cancer that contain high numbers of estrogen receptors (ERs). These constructs will be tested initially in the breast cancer line MCF7, and later in other ER positive breast cancer cell lines. We will also test the efficacy of our constructs in parallel experiments using ER minus breast cancer cell lines.

Example 12

Transfection experiments to test the ability of overexpressed cyclin D1 to block the tumorigenic potential of cancer cells in vivo.

When we have defined the levels of cyclin D1 expression that are required to block the growth of normal and transformed cells in vitro we will use a mouse model of tumor formation to test the ability of the human cyclin D1 protein to block the growth of mouse tumor cells in vivo. Tumorigenic mouse cell lines will be transfected with a G418-selectable, steroid-inducible construct encoding the cyclin D1 gene. Cells will be grown in the absence of steroid hormone (using dialysed serum) to enable cell growth and selection of transfected cells in vitro. Once stable cell lines containing either inducible cyclin D1 expression constructs or control constructs are isolated they will be injected into nude mice to determine if overexpression of cyclin D1 is capable of blocking the growth of tumor cells in vivo. Lines containing constructs lacking cyclin D1 will serve as negative controls.

Example 13

Generating transgenic mouse lines containing cyclin D1 expression constructs that are driven by cell type-specific promoter-enhancer sequences.

As a tool to test the contribution of specific cell types to subsequent developmental cell lineages, cyclin D1 expression constructs driven by tissue and cell type specific enhancers will be microinjected into mouse embryonic stem (ES) cells and these cells will be subsequently injected into developing mouse embryos. By the selection and engineering of appropriate enhancer elements into D1 expression constructs it should be possible to target precisely the cell populations in which cyclin D1 is expressed at high levels. This will have the effect of inducing such cells to enter a quiescent state such that they are subsequently unable to contribute to the development of specific cell lineage. Data regarding the lineages of particular cell types will prove useful for understanding the growth and differentiation potentials of various types of "dedifferentiated" cancer cells such as lymphoblasts, neuroblasts etc. Information generated in this manner should therefore help to provide additional criteria that will be valuable clinically for aiding in the selection of appropriate cancer treatments.

Example 14
Generation of monoclonal and polyclonal antibodies for quantitating the levels of cyclin D1 in tissue samples.

It is often crucial to be able to determine the growth state of cells within tissue samples when performing diagnostic tests upon suspected hyperplasias and neoplasias. We have shown that there is a very strong correlation between the levels of cyclin D1 protein and the ability of cells to grow in response to mitogens. We will develop a simple immunological method for estimating cyclin D1 levels and therefore the fraction of cells capable of proliferating in pathological specimens. Currently the presence of high levels of proliferating cell nuclear antigen (PCNA) is used as an estimate of proliferative ability. Since the absence of cyclin D1 is also associated with cell growth, such an assay would provide an essential corroborative method for estimating with a much higher level of confidence, the proportion of cells within fixed tissue sections that are in a quiescent versus proliferative state. We will elicit immune responses in mice (for the production of monoclonal antibodies) and in rabbits (for production of polyclonal antibodies).

Example 15
Targeting cyclin D1 expression constructs to tumor cells in vivo.

Mouse tumor cells will be transfected in vitro with expression constructs encoding a surface antigen used by bovine papilloma virus (BPV) to infect cells. Use of bovine virus should avoid the problem of selectively targeting tumor cells for viral infection as only cells expressing suitable surface receptor antigens being infected. A non-transforming, replication-deficient BPV construct encoding a constitutively expressed cyclin D1 gene will also be engineered. This construct will be tested for its ability to selectively infect tumorigenic mouse cells that express the surface antigen mentioned above. Initial tests of the ability of the recombinant virus to selectively infect cells expressing surface antigen will be done using mixed populations of tumorigenic cells that express the surface antigen at different levels. The expected result is that addition of the virus to such a mixed population of cells would result in only those cells expressing surface antigen would be infected. Only infected cells would express high levels of cyclin D1 and so we would expect that within 1–3 cells subcultivations, cells expressing surface antigen would be strongly selected against and would be lost from the cell culture. We should therefore be able to demonstrate the selective elimination of surface antigen-tagged tumor cells by growth inhibition due to the expression of high levels of cyclin D1. Surface antigens that occur naturally on different classes of human cancer cells will be identified. These antigens will be used in a similar manner, most likely utilizing a human adenovirus vector to attempt to target selectively cyclin D1 expression to tumor cells.

Modification of the above-described modes of carrying out various embodiments of this invention will be apparent to those skilled in the art following the teachings of this invention as set forth herein. The examples described above are not limiting, but are merely exemplary of this invention, the scope of which is defined by the following claims.

What is claimed:

1. A method for changing proliferation of mammalian cells in vivo comprising:

a) selecting said mammalian cells whose proliferation is to be changed; and b) changing the expression of cyclin D1 in said mammalian cells by the use of a genetic construct ex vivo, wherein the expression of cyclin D1 is decreased to increase cell proliferation or increased to decrease cell proliferation wherein said cells with changed expression of cyclin D1 show said change in proliferation when implanted in vivo.

2. The method of claim 1 wherein said mammalian cells are selected from the group consisting of normal cells and cancerous cells.

3. The method of claim 1 wherein said change in cell proliferation is increasing cell proliferation and said change in the expression of cyclin D1 is decreasing the expression of cyclin D1.

4. The method of claim 1 wherein said change in cell proliferation is decreasing cell proliferation and said change in the expression of cyclin D1 is increasing the expression of cyclin D1.

5. The method of claim 4 wherein said increasing said expression of cyclin D1 comprises introducing into said mammalian cells at least one composition selected from the group consisting of cyclin D1 and nucleotides which code for cyclin D1.

6. The method of claim 4 wherein said decreasing proliferation is blocking the proliferation of cancer cells.

* * * * *